United States Patent [19]

Driscoll et al.

[11] 3,972,941

[45] Aug. 3, 1976

[54] CHEMICAL REACTION PRODUCTS OF POLYISOBUTYLENE

[75] Inventors: Gary L. Driscoll, Boothwyn; Marcus W. Haseltine, Jr., Brookhaven, both of Pa.

[73] Assignee: Sun Oil Company, Philadelphia, Pa.

[22] Filed: Apr. 19, 1971

[21] Appl. No.: 135,295

[52] U.S. Cl. .................. 260/593 R; 260/601 R; 260/533 R; 260/533 C; 260/632 R; 260/465.3; 252/52 R; 252/73; 252/48.6; 252/49.8; 252/546; 260/597 R
[51] Int. Cl.² ............................... C07C 49/06
[58] Field of Search ............. 260/593 R, 597 R, 597

[56] References Cited
UNITED STATES PATENTS

| | | | |
|---|---|---|---|
| 2,824,896 | 2/1958 | Surmatis | 260/593 R |
| 3,715,313 | 2/1973 | Haseltine et al. | 252/52 |

*Primary Examiner*—James O. Thomas, Jr.
*Assistant Examiner*—James H. Reamer
*Attorney, Agent, or Firm*—Donald R. Johnson; J. Edward Hess; Richard P. Maloney

[57] ABSTRACT

Novel compositions, useful as additives to lubricants, are produced by reaction of various reagents with novel polyisobutylene oligimers containing at least one pair of maximally crowded geminal methyl groups. For example, ozonolysis of the novel polyisobutylenes can produce oxygenated derivatives (ketones, esters, alcohols, etc.) which are useful as components of traction fluids. One such alcohol is 1,1,3,3,5,5,7,7-octamethyl-1-octanol, which has been identified by its NMR spectrum and that of its complex with Eu(DPM)₃. Other novel compounds are 4,4,6,6,8,8-hexamethyl-2-nonanone and 2,2,6,6,8,8-hexamethyl-4-nonanone.

2 Claims, 5 Drawing Figures

EUROPIUM COMPLEX OF KETONE (II)

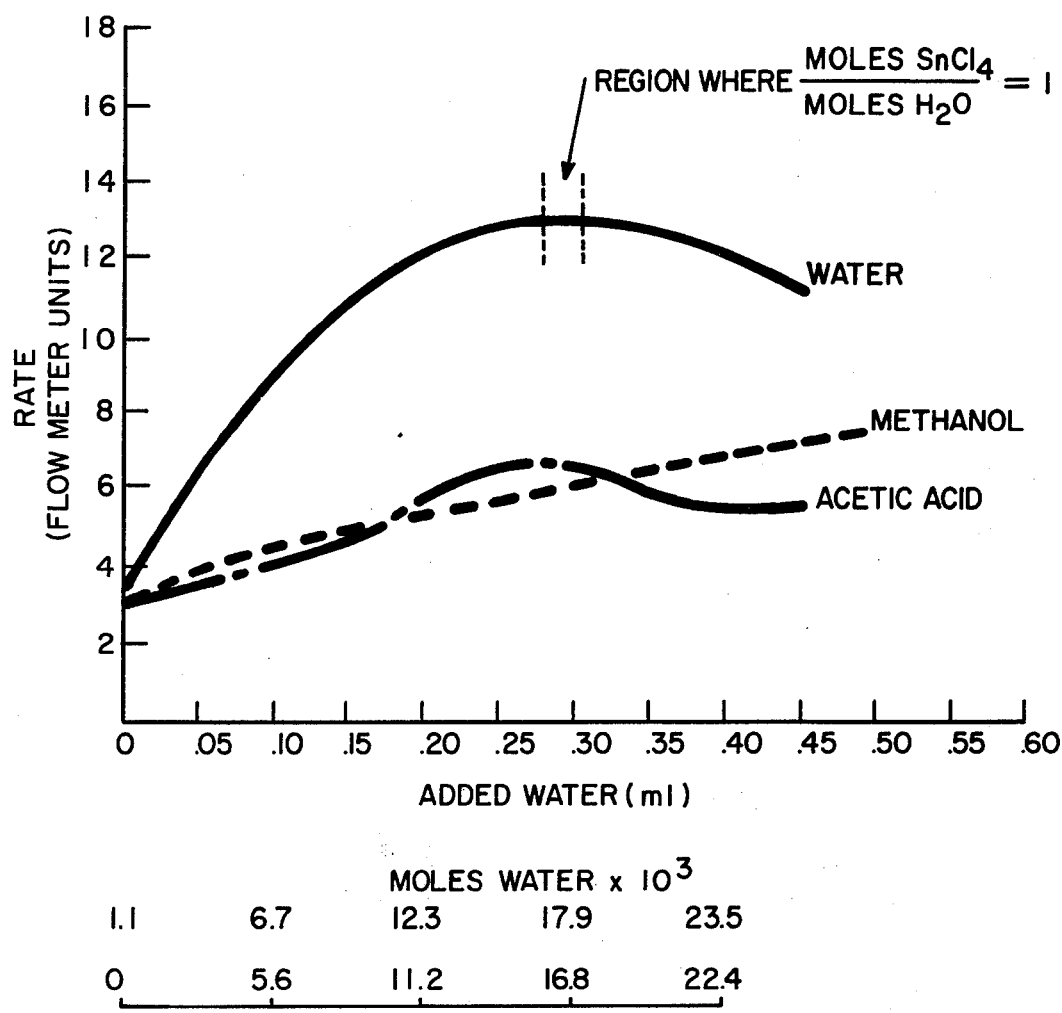

CHEMICAL REACTION PRODUCTS OF POLYISOBUTYLENE

CROSS REFERENCE TO RELATED APPLICATIONS

In commonly-owned copending application Ser. No. 52,301, filed July 6, 1970, (now U.S. 3,778,487 issued 12-11-73) of Gary L. Driscoll, Irl N. Duling and David S. Gates, novel polyolefin and hydrogenated polyolefin oils are described which are useful as traction fluids, or as components of traction fluids. In particular, said application discloses oils consisting essentially of isobutene oligimers in the $C_{12}$–$C_{48}$ carbon number range. The novel polyolefin oils or the individual olefins therein are also disclosed as being useful as chemical intermediates to prepare novel polar components (such as alcohols, acids, esters, ketones, thioketones, amides, amines, thioesters, phosphate esters of the alcohols and thioesters). The ketones, and other non-acidic ozonolysis products are disclosed as being useful as traction fluids or as components of traction fluids. Said application which is incorporated herein, also contains a declaration that such derivatives, and their use as traction fluids or as antiwear additives in lubricants are the invention of Gary L. Driscoll and Marcus W. Haseltine, Jr., the present applicants.

Said application further declares that the processes for preparation of said ozonolysis products are the invention of Gary L. Driscoll. One such process, disclosed in said application, involves mixing the polyolefin oil with about 3 volumes of acetic acid or methanol and adding ozone thereto. The reaction can be effected in the range of –80°–100°C. (preferably 0°–80°C.). The amount of ozone can be about one molecule of ozone per each double bond in oil. After reaction of the double bond with the ozone, an excess of water or hydrogen peroxide is added to hydrolyze the ozonolysis products. About one volume of water per volume of oil is sufficient to produce a mixture comprising acids and ketones.

Also relevant, and incorporated herein is Ser. No. 052,300, filed July 6, 1970, now U.S. Pat. NO. 3,775,503 issued Nov. 21, 1973.

A later-filed application, Ser. No. 144,165 filed May 17, 1971 (now U.S. Pat. No. 3,715,313, issued Feb. 6, 1973) contains additional description of the utility of the polar isobutylene compounds (e.g., the ketones) as traction fluids or as components of traction fluids.

SUMMARY OF THE INVENTION

Broadly, the present invention involves novel compositions comprising novel chemical compounds which can be produced by the action of various chemical reagents on the polyolefins or polyolefin oils of the aforementioned applications Ser. No. 52,300 now U.S. Pat. No. 3,775,503 and Ser. No. 52,301 now U.S. Pat. No. 3,778,487. Such compounds are useful as lubricant additives, particularly lubricants for tractive drives and limited slip differentials.

For example, one embodiment of the invention is a composition consisting essentially of an oxygen-containing chemical compound of a branched olefin hydrocarbon having 4N carbon atoms where N is an integer from 4–30, said olefin hydrocarbon having the formula:

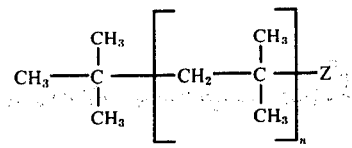

wherein $n$ is an integer from 3 to 29 inclusive, and wherein Z is:

(A) 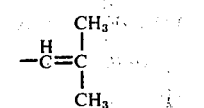

or (B) 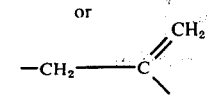

or (C) 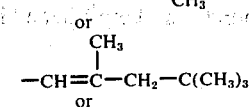

or (D) 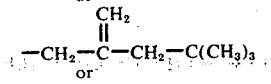

or (E) 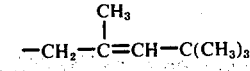

For example, such a novel compound is produced when said olefin is split at the double bond to produce two fragments, each said fragment having a carbonyl group at the site of the original attachment. Other novel compounds can be produced by further reaction of one of said fragments, said reaction involving either further fragmentation (e.g., decarboxylation), further oxidation, or both.

Ozonolyses of the olefin is one means of producing said compositions. Various novel compounds and compositions can be produced depending upon the nature of the olefin. For example, when Z is (A), such compounds can be produced by at least one of the following reactions (for convenience in reproduction, the ozone reactant, e.g., see Example 2, is not shown):

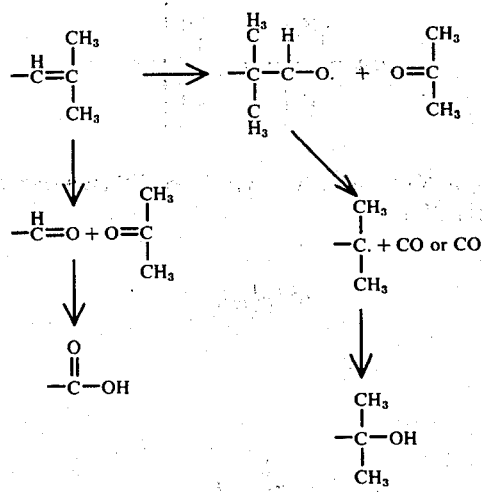

or when Z is (B), said compounds can be produced by the reaction:

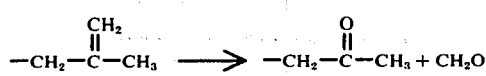

or when Z is (C) such compounds can be produced by at least one of the reactions:

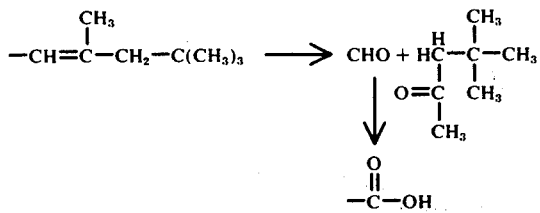

or when Z is (D) such compounds can be produced by the reaction:

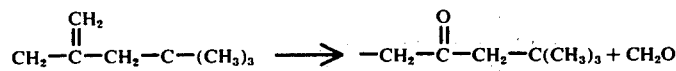

or when Z is (E) said compound is produced by at least one of the reactions:

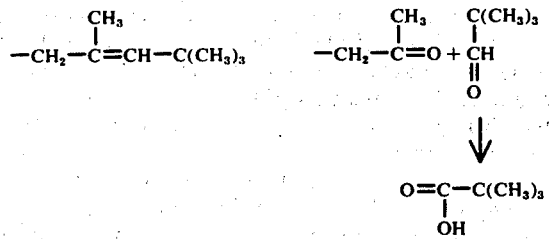

The novel oxygen containing compounds can have the structural formula

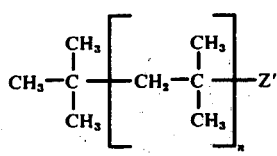

where n is an integer from 3 to 29 inclusive and wherein Z' is

or

or

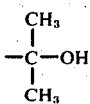

or

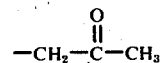

or

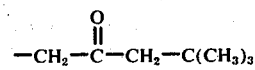

Typically, compositions can be obtained which contain 85–99 weight percent of one or a mixture of such novel compounds.

The novel substituted polybutenes of the present invention are usually liquids and have good solubility in petroleum oils. Therefore, these derivatives can be especially useful as lubricant additives or as additives to other oils, or petroleum products, (such as rubber process oils, hydraulic fluids, fuels, refrigeration oils, textile machinery lubricants, coolant for a nuclear reactor, paints, etc.). By choice of the molecular weight (or viscosity) of the polyolefin starting material the derivatives can be "tailored" to a desired viscosity or molecular weight.

BRIEF DESCRIPTION OF THE DRAWINGS

In the accompanying drawings,

FIG. 5 illustrates the acceleration of the polymerization rate of isobutylene (in a catalyst system comprising SnCl$_4$ and a solvent) which can be obtained by addition of a reaction promoting quantity of a reagent containing at least one hydroxyl group (e.g., H$_2$O, alcohol, carboxylic acid, etc.).

ILLUSTRATIVE EXAMPLES

EXAMPLE 1

Figure 1:
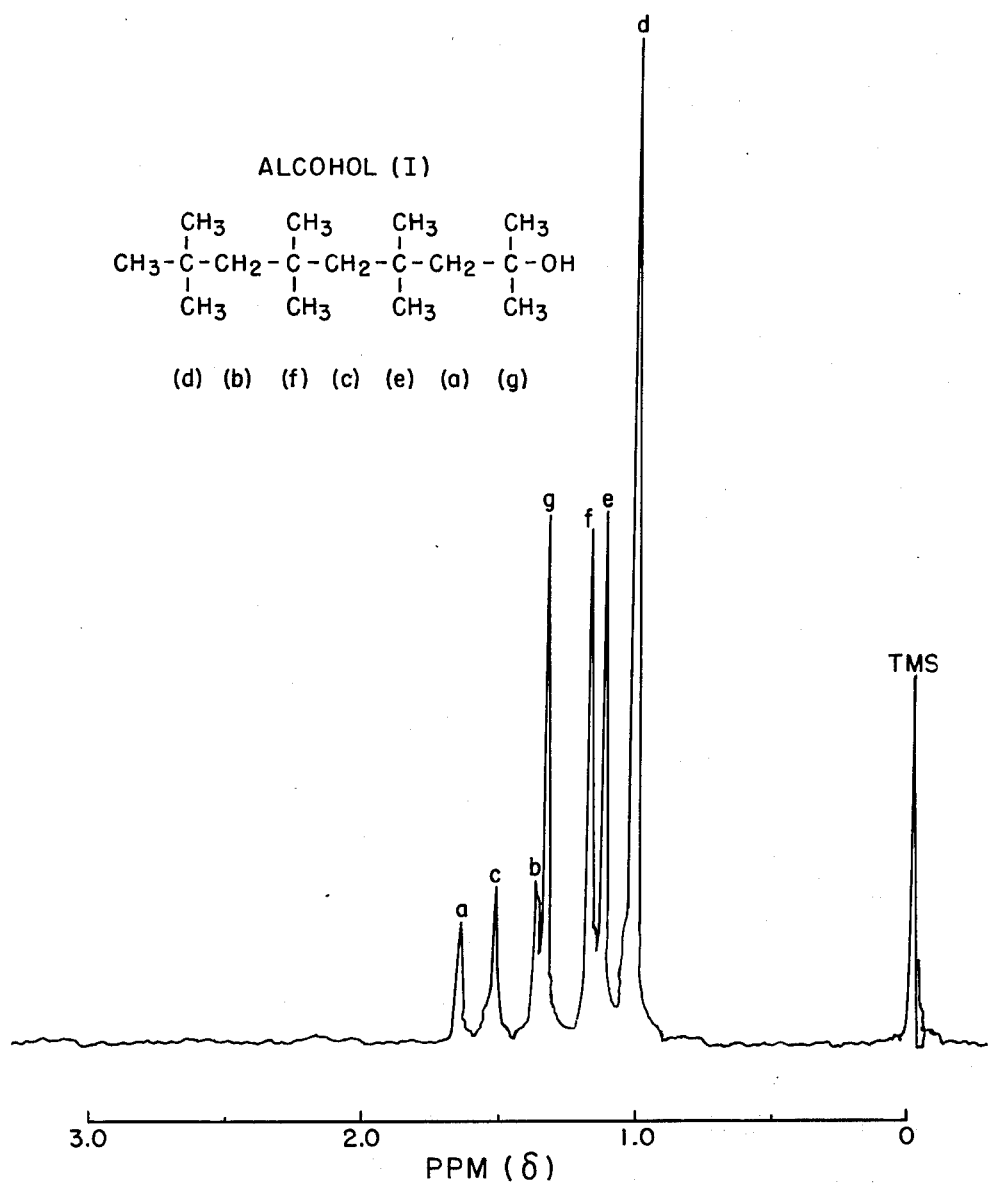
FIG. 1 is the nuclear magnetic resonance (NMR) spectrum of a novel alcohol (1,1,3,3,5,7,7-octamethyl-1-octanol) TMS indicates the internal standard, tetramethylsilane.

A three-necked, one-liter, round-bottomed flask was equipped with a mechanical stirrer, a gas inlet tube (which also serves for intermittent product removal), and a reflux condenser containing a thermometer which dipped into the liquid layer and was capped with a gas exit tube leading through a mercury bubbler to the atmosphere. Nitromethane (200 ml.) and stannic chloride (5 ml. = 11.15 g.) were added to the flask and the isobutylene flow started. The reaction was maintained at 30° ±1°C. with an ice bath. The rate of isobutylene addition was 7.2 g/min. which resulted in 8.5 ml/min. of product (density ~0.85) formation. At 20 min. intervals, the isobutylene feed and the stirrer were stopped and the layers permitted to separate. The top oil layer (170 ml.) was removed and the nitromethane (bottom) layer was returned to the reactor with 5 ml. (3% of product volume) fresh nitromethane added to compensate for solubility losses. After four 20 minute runs, the reaction was stopped The catalyst in the nitromethane layer was readily killed with water with some production of HCl fumes. No difficulty with an exotherm was encountered when killing the catalyst. The combined oil layers (665 ml. including 20 ml. nitromethane) were washed with water, with 5% sodium hydroxide solution, and twice more with water. A solvent such as pentane or hexane can be added to facilitate handling.

Although the oil of this example contains all of the novel polyisobutylene oligimers in series $C_{16}-C_{20} \ldots C_{48}+$, fraction vacuum distillation can be used to obtain fraction relatively pure in a given oligimer (e.g. $C_{16}$).

In the reaction of this example small amounts of water in the catalyst and/or feed material can act as a reaction promoter. If extremely pure materials are used in the process, a small amount of water ca be added to initiate or hasten the reaction. A lower alcohol (e.g., methanol) or acid (e.g., acetic acid) can also be used as such a promoter. Generally, the reaction rate can be increased (over anhydrous) by addition of 0.1–1.5 moles $H_2O$ per mole of $SnCl_4$. FIG. 5 illustrates the acceleration of the polymerization rate which can be obtained by such addition of a reaction promoter.

Polyolefin products, such as that of this example, can contain residual tin and chlorine (e.g., 250–5000 ppm Cl). As is discussed in more detail hereinaftr, these elements, particularly the tin, can be present as a metal-organic compound which imparts EP (extreme pressure lubricant) properties to the product. However, if one desires, the chlorine (e.g., 2000 ppm) can be removed from the product by heating the product with calcium oxide (lime) followed by filtration. Mild catalytic hydrogen treatment (e.g. 200 psi. of $H_2$, 200°C., Harshaw NI-0104P catalyst) can also be used to reduce the tin and chlorine content to very low levels (e.g., Cl from 2000 ppm. to 6 ppm.).

The process of the present example can also be used to convert butadiene to trans-1,4- and 1,2-polybutadienes. This is surprising since prior art cationic catalyst systems convert butadiene to cyclized polymers. Oxygenated derivatives of these polybutadienes can be obtained by ozonolysis as in the process of the next example.

1-Decene can also be polymerized with the catalyst system of the present example, particularly to get high yields of a low viscosity oil. Oxygenated derivatives of these poly 1-decenes can be obtained by ozonolysis in a similar manner to the process of the next example.

EXAMPLE 2

Polyisobutylene oil from Example 1 (260 ml., 221.4 g.) and anhydrous methanol (800 ml.) were placed in a three-necked, two-liter, round-bottomed flask equipped with a gas inlet tube, a mechanical stirrer, and a reflux condenser. The flask was maintained at about 0°C. by means of an ice bath while an oxygen-ozone stream (5.2 millimoles $O_3$ per minute was passed through for 150 minutes. After this time distilled water (300 ml.) was added and the mixture heated to reflux for 90 minutes. The oil layer was diluted with pentane (500 ml.) and successively extracted with about 250 ml. of water (twice); 5% ferrous sulfate solution; 5% sodium carbonate solution; water; 5% sodium carbonate solution; and water (twice).

The combined sodium carbonate and water extracts were acidified with concentrated hydrochloric acid and extracted with ether. After drying, the ether was removed to recover 8 g. (3.6%) of an acidic fraction.

The main pentane layer was dried over calcium chloride and the pentane removed on a steam bath to recover 194 g. (87.6% by weight) of a neutral fraction. The infrared spectral analysis of this material showed that it contained mainly carbonyl (aldehyde or ketone) functionally with smaller amounts of hydroxyl functionality. Analysis by gas-liquid chromatography showed that the composition of the product was essentially a repeating pattern of three major components in a given molecular weight range. (It is possible that other components were not separated using 6' silicone oil columns and 6' polyethylene glycol columns). Several minor components were also detected. Very little unreacted oil was present.

EXAMPLE 3

The neutral product of Example 2 was tested for its traction using a modified Roxana Four-Ball tester. It showed a traction higher than the original polyisobutylene (about 85 g. of torque versus about 72 g. initially) and higher than for commercially available polybutenes (about 66 g. of torque). This indicates that the product is useful as a traction fluid or as a component of a traction fluid.

EXAMPLE 4

The neutral product of Example 2 was distilled under vacuum and separated into several fractions. One of these fractions was collected over the range of 80°C. to 110°C. at 0.8 mm. Hg pressure. This fraction contained relatively few components. The invividual components were isolated by gas-liquid chromatography and characterized by means of infrared, mass, and nuclear magnetic resonance spectral data. The predominant component was

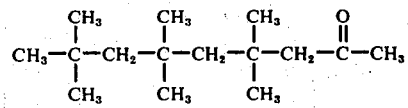

4,4,6,6,8,8,-hexamethyl-2-nonanone. Two lesser components were identified as

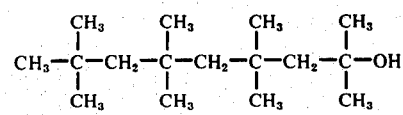

1,1,3,3,5,5,7,7-octamethyl-1-octanol and

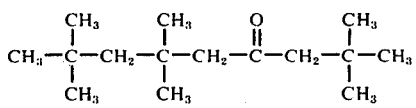

2,2,6,6,8,8-hexamethyl-4-nonanone.

The structural formulae of higher boiling fractions correspond to the above structures with an additional appropriate number (e.g., up to a total carbon number of at least about 49 for the ketones and at least about 50 for the alcohols) of

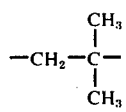

units inserted after the first t-butyl group.

EXAMPLE 5

The neutral product (50 g.) of Example 2 was dissolved in 200 ml. of diethyl ether and reacted with an excess of lithium aluminum hydride (8.0 g.) for four hours at reflux. The excess hydride was decomposed by reaction with ethyl acetate and 200 ml. of 15% hydrochloric acid was added cautiously. The ether layer was extracted twice with 250 ml. of water, dried over calcium chloride and the ether removed on a steam bath. The oily product (48 g., 96% by weight) was characterized as an alcohol by its infrared spectrum. No carbonyl absorption remained. Its gas-liquid chromatogram showed a repetition of two major peaks, the components having the same molecular weight no longer being separated by this column (6 feet of silicone rubber).

The alcohols which contain a large non-polar portion and a very polar alcohol portion are useful as solvents and especially as components in solvents for polymers such as polystyrene and polymethylmethacrylate. They are also useful as intermediates in the preparation of the corresponding acetate esters.

EXAMPLE 6

The alcohols of Example 5 (20 g.) were mixed with an excess (30 ml.) of acetic anhydride and heated on a steam bath for one hour. Excess water (100 ml.) was added to decompose the excess acetic anhydride. The mixture was heated for an additional hour. Ether (100 ml.) was added and the ether layer separated. The ether layer was extracted twice with approximately 100 ml. portions of water and then dried over calcium chloride. After the ether was removed, an infrared spectrum was obtained on the remaining 20 g. (100% by weight) of oil. The infrared spectrum showed the process of carbonyl groups (ester) and the substantial absence of hydroxyl groups (alcohol). This ester was useful as a traction fluid, both alone and in blends (as with hydrogenated polyolefin oils or hydrogenated paraffinic or naphthenic lubes or with synthetic naphthenes or adamantanes). The ester is also useful as a component of a gear lube, especially a lubricant for a limited slip differential. Typically blended fluids or lubes can contain in the range of 1–95% of such an ester.

EXAMPLE 7

A solution was prepared in a two-liter flask by mixing hydroxylamine hydrochloride (100 g.), water (600 ml.), 10% sodium hydroxide solution (400 ml.), and ethanol (400 ml.). This mixture was stirred while the neutral ketone product (40 ml., 34 g.) prepared according to Example 2 was added. The resulting mixture was heated and stirred at 80°C. for 30 minutes. The entire mixture was diluted with 1000 ml. water and extracted with 500 ml. ethyl ether. The ether layer was extracted twice more with 500 ml. portions of water. The ether layer was dried over calcium chloride and the ether removed on a steam bath. The resulting oil 28 g. (82.4% by weight) was found by infrared spectroscopy to contain oxime functions and substantially no unreacted carbonyl functionality. This oxime is soluble in paraffinic and naphthenic petroleum oils and is useful as a viscosity stabilizer for oil-extended unvulcanized rubber stock.

EXAMPLE 8

A three-liter, round-bottomed flask was equipped with a gas inlet tube, a mechanical stirrer, and a reflux condenser. This was charged with acetic acid (1500 ml.) and polyisobutylene oil (500 ml.) prepared according to Example 1. An oxygen-ozone stream (5 liters per minute, 5.3 millimoles ozone per minute) was passed through the mixture for 240 minutes. The temperature was maintained in the range of 25°–50°C. by means of a water bath. The reaction mixture was initially two phases, but became homogeneous near the end of the reaction time.

The crude mixture was heated to 90°–100°C. and 30% hydrogen peroxide solution (500 ml.) was added cautiously over a period of 50 minutes. The mixture was then refluxed (ca 110°C.) for 6 hours. Ether (1000 ml.) and water (150 ml.) were added and the layers separated after stirring. The ether layer was washed twice with water and twice with 0.2% ferrous sulfate solution (500 ml. each). The ether layer was next washed with 10% sodium carbonate solution (500 ml.) and twice with water (1000 ml. each time). Since the sodium salt of the acid is much more soluble in water than in sodium carbonate solution, most of the separation occurs in the two water washes. The remaining ether layer was dried over calcium chloride and the ether removed on a steam bath to give the neutral ketonic fraction. Gas-liquid chromatography and infrared spectroscopy indicated that the product was similar to the product of Example 2, but more complex and showing indications of significant isomerizations. This neutral fraction amounted to 232 g. (55.0% by weight).

The sodium carbonate extract and the two following water extracts were combined and made acidic by catious addition of excess hydrochloric acid and extracted with diethyl ether (500 ml.) The ether layer was dried over calcium chloride and the ether removed on a steam bath. The resulting liquid acid fraction weighed 134 g. (32.3% by weight). The infrared spectrum showed the absorbance bands characteristic of carboxylic acid functions.

EXAMPLE 9

The sodium salt of the acidic fraction can be readily obtained by proceeding according to Example 8 to the first water extraction following the 10% sodium carbonate extraction. When these two extracts were mixed, a phase separated. This can be diluted with diethyl ether and the phases separated. Drying over calcium chloride and removal of the ether on a steam bath results in a viscous liquid product which has an infrared spectrum consistent with a sodium carboxylate.

This product is useful as a detergent, as a surface active agent, and as a solubilizing agent. At least 20% diethyl ether can be dissolved in water containing a few percent of this salt.

The sodium salt can also be prepared directly from the acid and a suitable base under nearly anhydrous conditions. Salts of other metals, e.g., lithium, calcium, magnesium, barium, zinc, and cobalt, can also be prepared in a similar manner. Such salts are useful in compounding greases, hydraulic oils, lube oils, etc.

All samples of this sodium salt obtained to date have been liquid and contained impurities. It is not clear whether or not the salt would be a liquid if it were entirely pure. On the other hand, none of the other derivatives prepared in this series were solids.

EXAMPLE 10

The acidic fraction prepared according to Example 8 (25 ml., 22.6 g.), methanol (220 ml.), and 96% sulfuric acid (30 ml.) were placed in a 500 ml. round-bottomed flask and refluxed for 6 hours. Water (200 ml.) and diethyl ether (200 ml.) were added and the layers separated. The ether layer was successively extracted with water, 10% sodium carbonate, and water using 200 ml. each time. The ether layer was dried over calcium chloride and the ether removed on a steam bath. The resulting neutral ester product weighed 18 g. (80% by weight). Gas-liquid chromatography showed the repeating pattern to be three major components at each general molecular weight level. The repetitions were characterized by the four-carbon

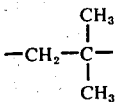

unit. Infrared analysis showed the absorbance expected for ester functionality and the absence of acid functionality.

The ester was useful as a traction fluid and as a component of blended traction fluids. Particularly useful blended base stocks comprise 1–99 volume % of the ester and from 99 to 1% of at least one naphthene or paraffin having an SUS viscosity at 100°F. in the range of 25–25,000.

EXAMPLE 11

An acid (1 g.) prepared according to Example 8 was mixed with thionyl chloride (1 ml.) and carefully warmed on a steam bath until the bubbling subsided. It was then heated and a nitrogen flow maintained while the thionyl chloride evaporated. Finally, a water aspirator-produced vacuum was applied to the solution which was maintained at 80°–90°C. for 5 minutes. An infrared spectrum on the oil product (which had a sharp odor) showed absorbance characteristics of acyl halides.

EXAMPLE 12

The acyl halide product of Example 11 was poured into methanol (25 ml.). Water (50 ml.) and diethyl ether (50 ml.) were added and the layers separated. The ether layer was extracted (once with 5% sodium carbonate (50 ml.) and twice with water (100 ml. each). The ether layer was dried over calcium chloride and the ether removed on a steam bath. The resulting oily product was shown by gas-liquid chromatography and infrared spectroscopy to be identical with the ester of Example 10.

EXAMPLE 13

An acid (50 g.) prepared according to Example 8 and excess (20 g.) of 85% hydrazine hydrate (the remaining 15% being water) were mixed in a 250 ml. Erlenmeyer flask with magnetic stirring. The mixture immediately became warm. The temperature was then raised by external heating to 125°C. and excess hydrazine fumed off in a well-ventilated hood. The temperature was maintained at 125°C. for 2 hours then raised to 185°–210°C. for a further 2 hours. An infrared spectrum of the very viscous material showed that it is substantially converted to the acyl hydrazide derivative. The product was dissolved in diethyl ether (400 ml.) and extracted twice with water (500 ml. each time). It was then extracted with 5% sodium carbonate solution (200 ml.) and twice with water (500 ml. each time). Many of these extractions resulted in serious emulsion difficulties. Such emulsions were broken with concentrated sodium chloride solution, but separation times of 1 to 2 days were still occasionally required. The ether layer was dried over calcium chloride and the ether removed on a steam bath.

The product was very viscous and light orange in color. An infrared spectrum was again determined and showed somewhat sharper bands. The material was especially characterized by absorbances near 3.1M and 6.1M typical of acyl hydrozides. This hydrazide was different from others because it was liquid rather than solid and was soluble in pentane, white mineral oil, and other hydrocarbons, but insoluble in water. This is to be contrasted with the hydrazide from oleic acid, which is solid and unsoluble in oil. Adipyl dihydrozide, acetyl hydrazide, and benzoyl hydrazide are also solids which are soluble in water but insoluble in hydrocarbons. The hydrazide of this example is especially useful as a viscosity stabilizer in oil-extended uncompounded synthetic rubbers of these solubility properties. It is also useful as an emulsifying agent and as an antiozonant in rubber.

EXAMPLE 14

The acid (10 g.) prepared in Example 8 was dissolved in methanol (50 ml.) containing added water (1 ml.) Sodium borohydride (3 g.) was added in small portions over 1 hour. Ether (100 ml.) and water (100 ml.) were added and the layers separated. The ether layer was extracted twice more with water (100 ml. each) and the ether layer discarded. The combined water layers were cautiously acidified with concentrated hydrochloric acid and ether (100 ml.) was added. The layers were separated. The ether layer was extracted with water (100 ml.), dried over calcium chloride, and the ether removed. The resulting acid was converted to its corresponding ester by the procedures of Examples 11 and 12. Gas-liquid chromatography showed that the middle component of the three major components described in Example 8 was considerably enhanced.

Since it is well known that sodium borohydride will not reduce carboxylic acids under these conditions but will reduce esters, ketones, and aldehydes, it is reasonable to conclude that the center and largest component represents the original acidic component and the other peaks represent other carbonyl components not separated due to the previously mentioned strong solubilizing power of the sodium salt of the carboxylic acid.

EXAMPLE 15

The neutral ketone (10 g.) prepared according to Example 2 was slowly added to 85% aqueous acetic acid (100 ml.) containing chromic acid (2 g.) heated on a steam bath to around 90°C. This was left for 2 hours with occasional shaking. Then water (200 ml.) and ether (200 ml.) were added. The ether layer was extracted with water, 10% hydrochloric acid, 10% sodium hydroxide solution, and twice with water. It was then passed over a 3 foot × 1 inch column of chromatographic grade alumina. The ether used for this elution was removed to leave a product of a dissolved salt of chromium (III). Gas-liquid chromatographic analysis showed that the resulting product was a substantially purified form of the indicated ketone.

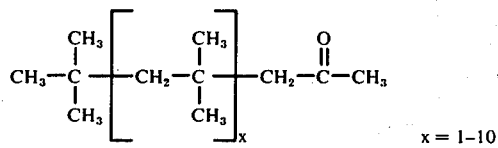

resulting from selective oxidation or complexation of the impurities.

EXAMPLE 16

This example deals with the use of the paramagnetic complex, europium (III) 2,2,6,6-tetramethylheptanedionate [tris(dipivalomethanato)-europium(III)], (referred to hereinafter as Eu(DPM)$_3$), as an NMR shift reagent and, thus, provides a means of characterizing novel oxygenated compounds, such as those of Example 4 and Example 15. Eu(DPM)$_3$ can be used to produce selective proton resonance shifts which accentuate chemical shift differences between geminal methyl and between isolated methylene groups, as in the highly branched alcohols and ketones.

The use of Du(DM)$_3$ as a complexing agent has been know to the art to produce selective shifts of porton resonances in the NMR spectrum of cholesterol and more recently, to simplify the NMR spectra of benzyl alcohol and n-hexanol. However, this example is the first report that this complexing reagent produces selective proton shifts for oxygenated species which are characterized by "crowded" and sterically hindered geminal methyl and isolated methylene groups. The 60-MHz NMR spectrum of one of these, 1,1,3,3,5,5,7,7-octamethyl-1-octanol (I) is given in FIG. 1. All of the proton assignments for this compound with the exception of the hydroxyl proton are included with this spectrum. Increased crowding of geminal methyl and isolated methylene groups results in a downfield shift of the resonance peaks for these protons with the most crowded groups occurring at the lowest field positions of their respective geminal methyl and methylene categories (see Ser. No. 52,300) now U.S. Pat. No. 3,775,503.

Figure 2:
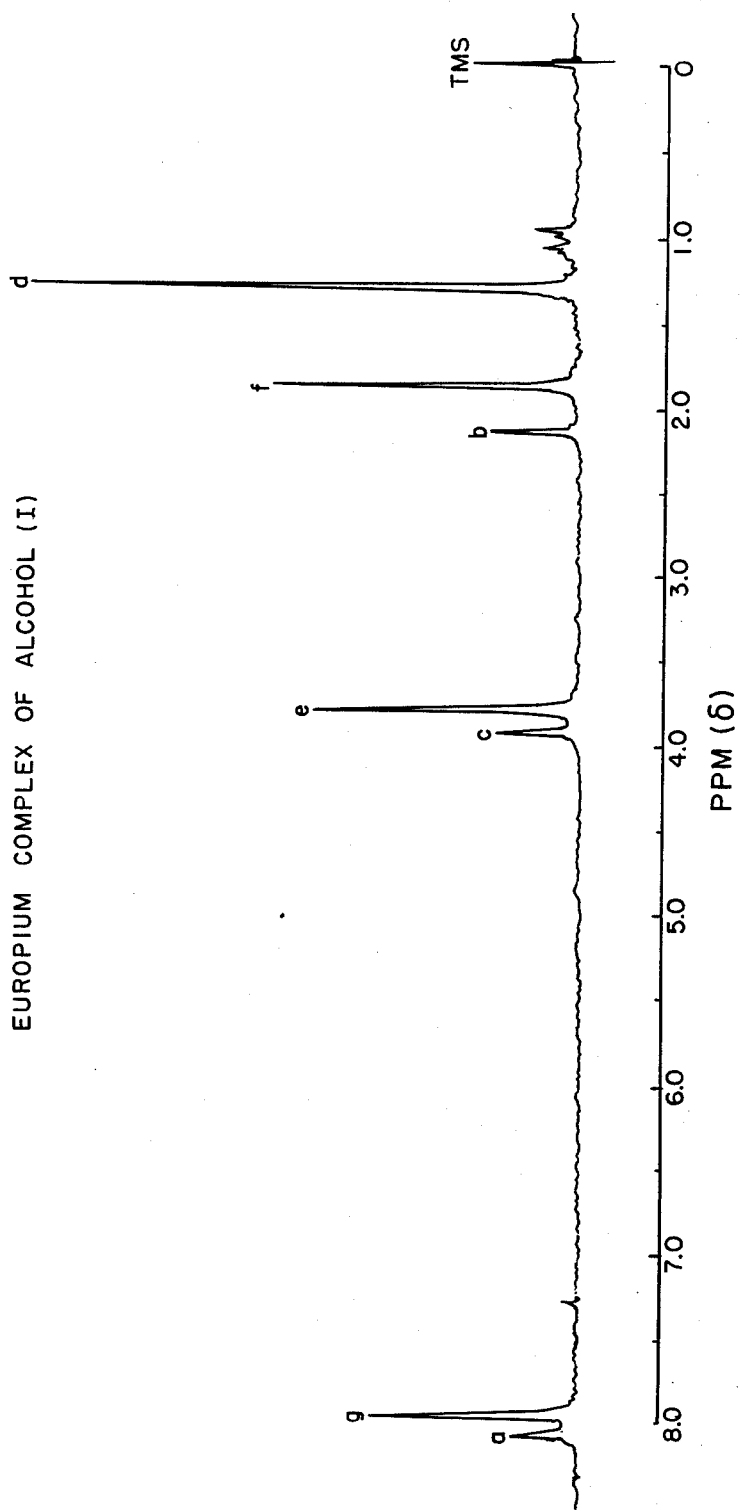
FIG. 2 is the NMR spectrum of the Europium Complex (i.e., with Eu(DPM)$_3$) of the alcohol of FIG. 1.
Figure 4:
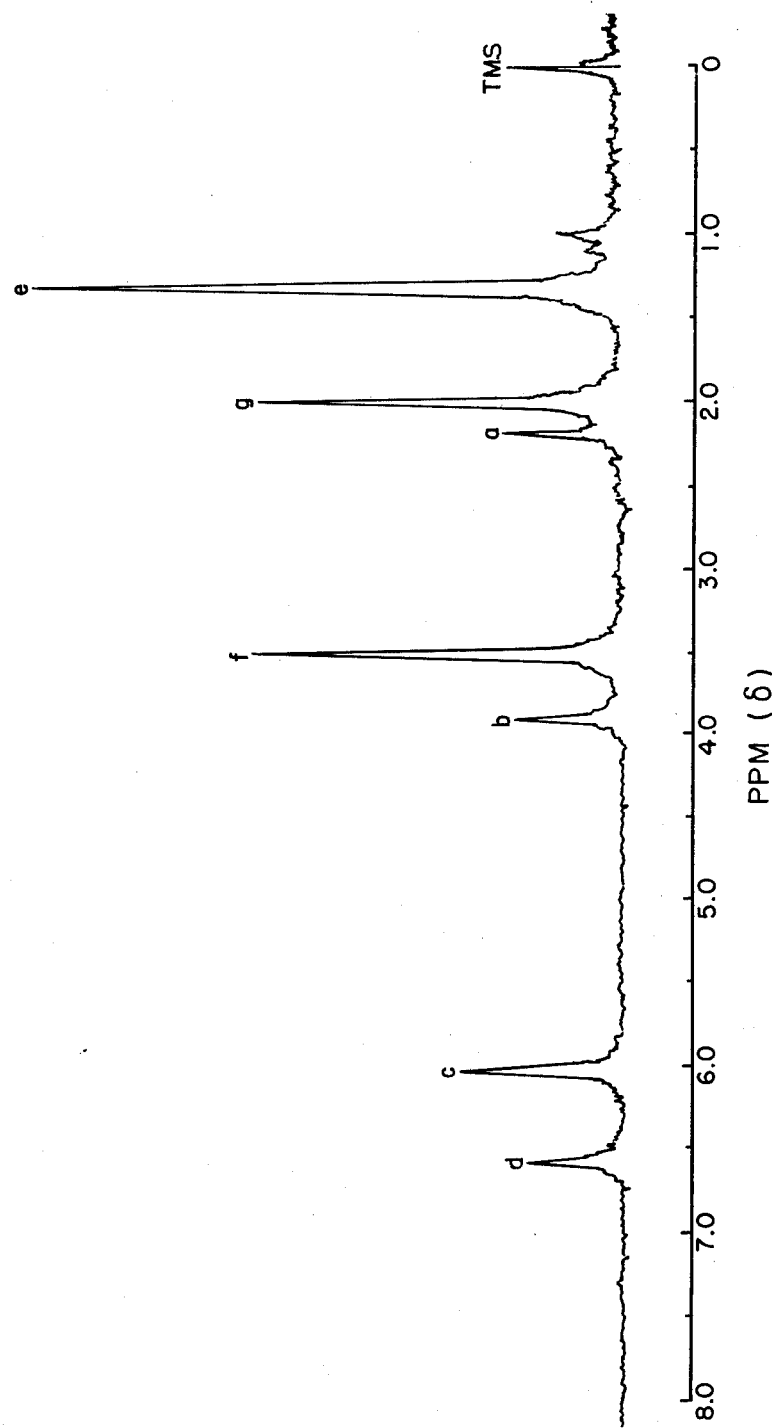
FIG. 4 is the NMR spectrum of the Europium Complex of the ketone of FIG. 3.

The NMR spectrum of the complexed alcohol is shown in FIG. 2. The weak resonance signals appearing in the 1.0 ppm. region of the spectra of the complexed species in FIGS. 2 and 4 are due to protons of uncomplexed material. Association of the alcohol species with Eu(DPM)$_3$ at the hydroxyl group gives induced shifts which significantly decrease with increasing distance of the protons from the hydroxyl group. In the uncomplexed spectrum of (I), all the proton resonance signals of the geminal methyl groups are upfield from the proton signals of the methylene groups, while in the spectrum of the complexed alcohol, field positions of these signals are interspersed with those of the methylene groups.

From the spectrum in FIG. 2 and the $R^{-3}$ interpretations of the paramagnetic shifts as given by Hinckley JACS 91, 5160 (1969), one can differentiate methylene and geminal methyl groups which are about the same distance from the paramagnetic ion center i.e., are the same number of carbon atoms removed from the point of association. Although these groups have essentially the same paramagnetic shifts, their individual proton resonance signals, as expected, are resolved of variations in local diamagnetic shielding. These results indicate that NMR studies using this complexing technique should prove valuable in the structure eluciation of even longer chain alcohols as well as of the more complex and highly unsymmetrical species.

Figure 3:
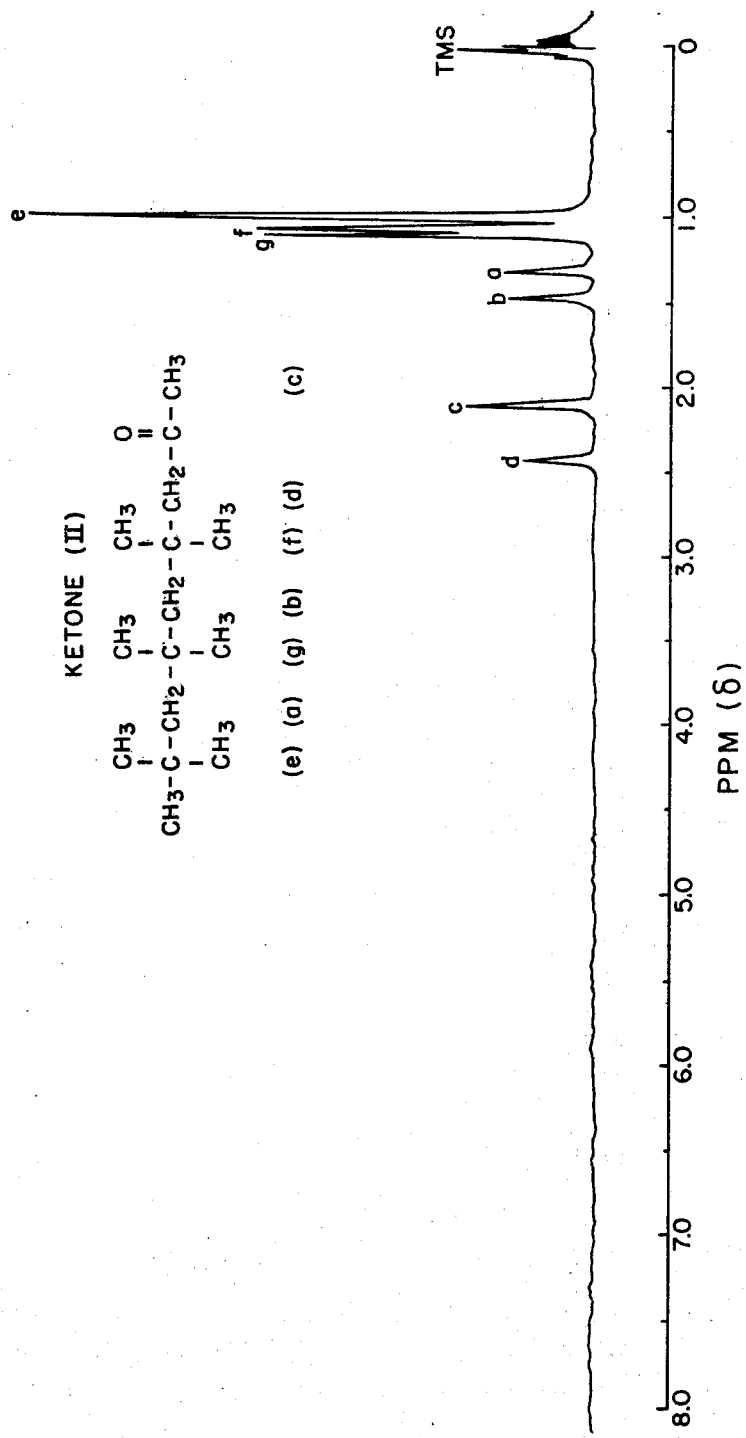
FIG. 3 is the NMR spectrum of a novel ketone (4,4,6,6,8,8-hexamethyl-2-nonanone).

The 60-MHz spectrum of a second oxygenated species, 4,4,6,6,8,8,-hexamethyl-2-nonanone (II) is given in FIG. 3 with proton assignments. This spectrum is also characterized by the most crowded geminal methyl and methylene group (excluding groups α to the C=O) occurring at the lowest field position. The NMR spectrum of the complexed ketone given in FIG. 4 shows inductive shifts which are comparable in magnitude with those obtained for the complexed alcohol species (I).

The NMR spectra of these examples were obtained on a Varian Model A-60 spectrometer at ambient temperatures (34° ± 1°C.) using deuterated chloroform, CDCl$_3$, as the solvent and about 1 percent of tetramethylsilane, TMS, as the internal standard. All spectra were run at a sweep width of 500 Hz. The alcohol species, FIG. 1, was recorded using a solution of 0.35 ml of solvent and 5.5 × 10$^{-5}$ moles of sample. The addition of 2.7 × 10$^{-5}$ moles of Eu(DPM)$_3$ to this solution gave the NMR spectrum shown in FIG. 2. The ketone spectrum, FIG. 3, was recorded using a solution of 9.35 ml of solvent and 8.8 × 10$^{-5}$ moles of sample. The spectrum of the complexed ketone, FIG. 4, resulted from the addition of 4.5 ×10 10$^{-5}$ moles of Eu(DPM)$_3$ to this solution. CDCl$_3$ appeared to be a better solvent than CCl$_4$ for dissolving the complexes of these oxygenated materials. The application of a small amount of heat also aided in effecting complete solution of the complexed material. The europium complex, Eu(DPM)$_3$ was obtained from Alfa Inorganics, Inc., Beverly, Mass. ("Eu-Resolve" -M.P. 188°–189°C).

EXAMPLE 17

The reaction product of Example 1 contains substantial amounts of tin and chlorine. Most probably, the tin and chlorine are chemically combined, in a highly soluble and compatible form, with one or more isobutylene oligimers. In any event, the recovered polyisobutylene oil can also contain such tin and chlorine. Such a novel tin and/or chlorine containing polyisobutylene oil has improved antiwear properties (e.g. a 4-ball tester "wear-scar" in the order of 0.4–0.6mm. compared to about 0.75mm. for a solvent refined paraffinic lube of comparable viscosity). Chemical derivatives (such as those of the preceeding Examples 2–6 and 10 can also exhibit improved antiwear properties, which can be caused in whole or in part by inclusion of such tin and chlorine or, perhaps, the improved antiwear properties may be, in whole or in part, an inherent property of said derivative.

An antiwear additive, e.g., for incorporation in conventional naphthenic distillates, hydrorefined lube hydrocracked oils, white oils, solvent refined paraffinic lubes or mixtures thereof, can be obtained from such reaction products (or tin and chlorine containing oils) by such means as extraction with a solvent (preferably acetone) for the presumed organo tin-chlorine complex. Preferred solvents comprise acetone, ethanol, methanol, methyl ethyl-ketone, dimethyl formamide, sulfolane, furfural, nitromethane, nitroethane, and the like) that is, solvents which will not dissolve the oil but will dissolve the more polar complex. Readily detectable antiwear protection is provided by such additives at concentration levels which impart 100 parts of tin per million parts of oil, with a typical range being 50 ppm.-10 weight percent of tin.

Therefore, one aspect of the present invention is novel lubricating oil additives comprising the tin-containing products of the polymerization of isobutylene using stannic chloride catalyst, such polymerizations being carried out between −80°C. and 100°C. at a pressure from 0–250 psia. These additives can contain from 0.005 to 50 weight percent tin.

These compositions can also be used as additives to fuels (e.g., diesel oil, gasoline and jet fuel) to preven wear.

The invention claimed is:

1. As a composition of matter a compound of the structural formula

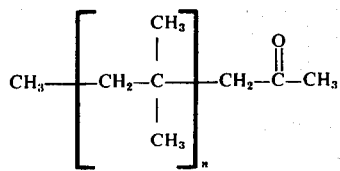

wherein *n* is an integer from 1 to 29 inclusive.

2. A composition according to claim 1 wherein said compound is 4,4,6,6,8,8-hexamethyl-2-nonanone.

* * * * *